United States Patent
Kopp et al.

(10) Patent No.: US 11,622,824 B2
(45) Date of Patent: *Apr. 11, 2023

(54) ROBOTIC SURGICAL SYSTEM TORQUE TRANSDUCTION SENSING

(71) Applicant: Covidien LP, Mansfield, MA (US)

(72) Inventors: Brock Kopp, Boulder, CO (US); Philip J. Irka, Madison, CT (US); Mark H. MacLeod, Brookfield, CT (US)

(73) Assignee: COVIDIEN LP, Mansfield, MA (US)

(*) Notice: Subject to any disclaimer, the term of this patent is extended or adjusted under 35 U.S.C. 154(b) by 136 days.

This patent is subject to a terminal disclaimer.

(21) Appl. No.: 17/179,573

(22) Filed: Feb. 19, 2021

(65) Prior Publication Data

US 2021/0186631 A1 Jun. 24, 2021

Related U.S. Application Data (63) Continuation of application No. 16/713,586, filed on Dec. 13, 2019, now Pat. No. 10,932,870, which is a
(Continued)

(51) Int. Cl.
*G01B 3/48* (2006.01)
*A61B 34/30* (2016.01)
(Continued)

(52) U.S. Cl.
CPC .............. *A61B 34/30* (2016.02); *A61B 34/76* (2016.02); *G01L 25/003* (2013.01);
(Continued)

(58) Field of Classification Search
CPC .................. A61B 34/30; A61B 34/76; A61B 2017/00128; G01L 25/003; G01R 31/343; H02K 11/20; H02K 11/24; H02P 29/02
See application file for complete search history.

(56) References Cited

U.S. PATENT DOCUMENTS 4,613,800 A * 9/1986 Jeppsson ................ H02K 11/24
318/434
5,063,316 A * 11/1991 E-Ming ................ H01H 35/006
310/68 B
(Continued)

FOREIGN PATENT DOCUMENTS

EP          2866716 A1    5/2015
JP      2005523174 A      8/2005
(Continued)

OTHER PUBLICATIONS

Australian Examination Report No. 1 dated May 11, 2021 corresponding to counterpart Patent Application AU 2016279993.
(Continued)

*Primary Examiner* — Muhammad S Islam
(74) *Attorney, Agent, or Firm* — Carter, DeLuca & Farrell, LLP (57) ABSTRACT

A method of verifying torque measurements of a reaction torque transducer of an instrument drive unit includes a controller receiving a verification signal, generating an acceptable range of torques, receiving a torque signal, comparing the torque signal to the acceptable range of torques, and stopping a motor if the torque applied by the motor is outside of the acceptable range of torques. The verification signal is indicative of the current drawn by the motor and the torque signal is indicative of torque applied by the motor.

20 Claims, 4 Drawing Sheets

Related U.S. Application Data continuation of application No. 15/579,308, filed as application No. PCT/US2016/037478 on Jun. 15, 2016, now Pat. No. 10,507,068.

(60) Provisional application No. 62/180,124, filed on Jun. 16, 2015.

(51) Int. Cl.
| | |
|---|---|
| *H02K 11/24* | (2016.01) |
| *H02P 29/02* | (2016.01) |
| *H02K 11/20* | (2016.01) |
| *G01L 25/00* | (2006.01) |
| *G01R 31/34* | (2020.01) |
| *A61B 34/00* | (2016.01) |
| *A61B 90/00* | (2016.01) |
| *H02K 11/27* | (2016.01) |
| *A61B 17/00* | (2006.01) |

(52) U.S. Cl.
CPC .......... *G01R 31/343* (2013.01); *H02K 11/20* (2016.01); *H02K 11/24* (2016.01); *H02P 29/02* (2013.01); *A61B 2017/00119* (2013.01); *A61B 2017/00123* (2013.01); *A61B 2017/00128* (2013.01); *A61B 2090/066* (2016.02); *H02K 11/27* (2016.01)

(56) References Cited

U.S. PATENT DOCUMENTS

| | | | |
|---|---|---|---|
| 5,327,790 A * | 7/1994 | Levin | B25J 9/12 |
| | | | 73/862.321 |
| 5,512,883 A | 4/1996 | Lane, Jr. | |
| 6,132,368 A | 10/2000 | Cooper | |
| 6,206,903 B1 | 3/2001 | Ramans | |
| 6,246,200 B1 | 6/2001 | Blumenkranz et al. | |
| 6,312,435 B1 | 11/2001 | Wallace et al. | |
| 6,331,181 B1 | 12/2001 | Tierney et al. | |
| 6,394,998 B1 | 5/2002 | Wallace et al. | |
| 6,424,885 B1 | 7/2002 | Niemeyer et al. | |
| 6,441,577 B2 | 8/2002 | Blumenkranz et al. | |
| 6,459,926 B1 | 10/2002 | Nowlin et al. | |
| 6,491,691 B1 | 12/2002 | Morley et al. | |
| 6,491,701 B2 | 12/2002 | Tierney et al. | |
| 6,493,608 B1 | 12/2002 | Niemeyer | |
| 6,565,554 B1 | 5/2003 | Niemeyer | |
| 6,645,196 B1 | 11/2003 | Nixon et al. | |
| 6,659,939 B2 | 12/2003 | Moll et al. | |
| 6,671,581 B2 | 12/2003 | Niemeyer et al. | |
| 6,676,684 B1 | 1/2004 | Morley et al. | |
| 6,685,698 B2 | 2/2004 | Morley et al. | |
| 6,699,235 B2 | 3/2004 | Wallace et al. | |
| 6,714,839 B2 | 3/2004 | Salisbury, Jr. et al. | |
| 6,716,233 B1 | 4/2004 | Whitman | |
| 6,728,599 B2 | 4/2004 | Wang et al. | |
| 6,746,443 B1 | 6/2004 | Morley et al. | |
| 6,766,204 B2 | 7/2004 | Niemeyer et al. | |
| 6,770,081 B1 | 8/2004 | Cooper et al. | |
| 6,772,053 B2 | 8/2004 | Niemeyer | |
| 6,783,524 B2 | 8/2004 | Anderson et al. | |
| 6,793,652 B1 | 9/2004 | Whitman et al. | |
| 6,793,653 B2 | 9/2004 | Sanchez et al. | |
| 6,799,065 B1 | 9/2004 | Niemeyer | |
| 6,837,883 B2 | 1/2005 | Moll et al. | |
| 6,839,612 B2 | 1/2005 | Sanchez et al. | |
| 6,840,938 B1 | 1/2005 | Morley et al. | |
| 6,843,403 B2 | 1/2005 | Whitman | |
| 6,846,309 B2 | 1/2005 | Whitman et al. | |
| 6,866,671 B2 | 3/2005 | Tierney et al. | |
| 6,871,117 B2 | 3/2005 | Wang et al. | |
| 6,879,880 B2 | 4/2005 | Nowlin et al. | |
| 6,899,705 B2 | 5/2005 | Niemeyer | |
| 6,902,560 B1 | 6/2005 | Morley et al. | |
| 6,931,330 B1 | 8/2005 | Yi et al. | |
| 6,936,042 B2 | 8/2005 | Wallace et al. | |
| 6,951,535 B2 | 10/2005 | Ghodoussi et al. | |
| 6,974,449 B2 | 12/2005 | Niemeyer | |
| 6,991,627 B2 | 1/2006 | Madhani et al. | |
| 6,994,708 B2 | 2/2006 | Manzo | |
| 7,048,745 B2 | 5/2006 | Tierney et al. | |
| 7,066,926 B2 | 6/2006 | Wallace et al. | |
| 7,118,582 B1 | 10/2006 | Wang et al. | |
| 7,125,403 B2 | 10/2006 | Julian et al. | |
| 7,155,315 B2 | 12/2006 | Niemeyer et al. | |
| 7,239,940 B2 | 7/2007 | Wang et al. | |
| 7,306,597 B2 | 12/2007 | Manzo | |
| 7,357,774 B2 | 4/2008 | Cooper | |
| 7,373,219 B2 | 5/2008 | Nowlin et al. | |
| 7,379,790 B2 | 5/2008 | Toth et al. | |
| 7,386,365 B2 | 6/2008 | Nixon | |
| 7,391,173 B2 | 6/2008 | Schena | |
| 7,398,707 B2 | 7/2008 | Morley et al. | |
| 7,413,565 B2 | 8/2008 | Wang et al. | |
| 7,453,227 B2 | 11/2008 | Prisco et al. | |
| 7,524,320 B2 | 4/2009 | Tierney et al. | |
| 7,574,250 B2 | 8/2009 | Niemeyer | |
| 7,594,912 B2 | 9/2009 | Cooper et al. | |
| 7,607,440 B2 | 10/2009 | Coste-Maniere et al. | |
| 7,666,191 B2 | 2/2010 | Orban, III et al. | |
| 7,682,357 B2 | 3/2010 | Ghodoussi et al. | |
| 7,689,320 B2 | 3/2010 | Prisco et al. | |
| 7,695,481 B2 | 4/2010 | Wang et al. | |
| 7,695,485 B2 | 4/2010 | Whitman et al. | |
| 7,699,855 B2 | 4/2010 | Anderson et al. | |
| 7,713,263 B2 | 5/2010 | Niemeyer | |
| 7,725,214 B2 | 5/2010 | Diolaiti | |
| 7,727,244 B2 | 6/2010 | Orban, III et al. | |
| 7,741,802 B2 | 6/2010 | Prisco et al. | |
| 7,756,036 B2 | 7/2010 | Druke et al. | |
| 7,757,028 B2 | 7/2010 | Druke et al. | |
| 7,762,825 B2 | 7/2010 | Burbank et al. | |
| 7,778,733 B2 | 8/2010 | Nowlin et al. | |
| 7,803,151 B2 | 9/2010 | Whitman | |
| 7,806,891 B2 | 10/2010 | Nowlin et al. | |
| 7,819,859 B2 | 10/2010 | Prisco et al. | |
| 7,819,885 B2 | 10/2010 | Cooper | |
| 7,824,401 B2 | 11/2010 | Manzo et al. | |
| 7,835,823 B2 | 11/2010 | Sillman et al. | |
| 7,843,158 B2 | 11/2010 | Prisco | |
| 7,865,266 B2 | 1/2011 | Moll et al. | |
| 7,865,269 B2 | 1/2011 | Prisco et al. | |
| 7,886,743 B2 | 2/2011 | Cooper et al. | |
| 7,899,578 B2 | 3/2011 | Prisco et al. | |
| 7,907,166 B2 | 3/2011 | Lamprecht et al. | |
| 7,935,130 B2 | 5/2011 | Williams | |
| 7,963,913 B2 | 6/2011 | Devengenzo et al. | |
| 7,983,793 B2 | 7/2011 | Toth et al. | |
| 8,002,767 B2 | 8/2011 | Sanchez et al. | |
| 8,004,229 B2 | 8/2011 | Nowlin et al. | |
| 8,012,170 B2 | 9/2011 | Whitman et al. | |
| 8,054,752 B2 | 11/2011 | Druke et al. | |
| 8,062,288 B2 | 11/2011 | Cooper et al. | |
| 8,079,950 B2 | 12/2011 | Stern et al. | |
| 8,100,133 B2 | 1/2012 | Mintz et al. | |
| 8,108,072 B2 | 1/2012 | Zhao et al. | |
| 8,120,301 B2 | 2/2012 | Goldberg et al. | |
| 8,142,447 B2 | 3/2012 | Cooper et al. | |
| 8,147,503 B2 | 4/2012 | Zhao et al. | |
| 8,151,661 B2 | 4/2012 | Schena et al. | |
| 8,155,479 B2 | 4/2012 | Hoffman et al. | |
| 8,182,469 B2 | 5/2012 | Anderson et al. | |
| 8,202,278 B2 | 6/2012 | Orban, III et al. | |
| 8,206,406 B2 | 6/2012 | Orban, III | |
| 8,210,413 B2 | 7/2012 | Whitman et al. | |
| 8,216,250 B2 | 7/2012 | Orban, III et al. | |
| 8,220,468 B2 | 7/2012 | Cooper et al. | |
| 8,256,319 B2 | 9/2012 | Cooper et al. | |
| 8,285,517 B2 | 10/2012 | Sillman et al. | |
| 8,315,720 B2 | 11/2012 | Mohr et al. | |
| 8,335,590 B2 | 12/2012 | Costa et al. | |
| 8,347,757 B2 | 1/2013 | Duval | |
| 8,374,723 B2 | 2/2013 | Zhao et al. | |

(56) References Cited

U.S. PATENT DOCUMENTS

| | | |
|---|---|---|
| 8,418,073 B2 | 4/2013 | Mohr et al. |
| 8,419,717 B2 | 4/2013 | Diolaiti et al. |
| 8,423,182 B2 | 4/2013 | Robinson et al. |
| 8,452,447 B2 | 5/2013 | Nixon |
| 8,454,585 B2 | 6/2013 | Whitman |
| 8,499,992 B2 | 8/2013 | Whitman et al. |
| 8,508,173 B2 | 8/2013 | Goldberg et al. |
| 8,528,440 B2 | 9/2013 | Morley et al. |
| 8,529,582 B2 | 9/2013 | Devengenzo et al. |
| 8,540,748 B2 | 9/2013 | Murphy et al. |
| 8,551,116 B2 | 10/2013 | Julian et al. |
| 8,562,594 B2 | 10/2013 | Cooper et al. |
| 8,594,841 B2 | 11/2013 | Zhao et al. |
| 8,597,182 B2 | 12/2013 | Stein et al. |
| 8,597,280 B2 | 12/2013 | Cooper et al. |
| 8,600,551 B2 | 12/2013 | Itkowitz et al. |
| 8,608,773 B2 | 12/2013 | Tierney et al. |
| 8,620,473 B2 | 12/2013 | Diolaiti et al. |
| 8,624,537 B2 | 1/2014 | Nowlin et al. |
| 8,634,957 B2 | 1/2014 | Toth et al. |
| 8,638,056 B2 | 1/2014 | Goldberg et al. |
| 8,638,057 B2 | 1/2014 | Goldberg et al. |
| 8,644,988 B2 | 2/2014 | Prisco et al. |
| 8,666,544 B2 | 3/2014 | Moll et al. |
| 8,668,638 B2 | 3/2014 | Donhowe et al. |
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,758,352 B2 | 6/2014 | Cooper et al. |
| 8,761,930 B2 | 6/2014 | Nixon |
| 8,768,516 B2 | 7/2014 | Diolaiti et al. |
| 8,786,241 B2 | 7/2014 | Nowlin et al. |
| 8,790,243 B2 | 7/2014 | Cooper et al. |
| 8,808,164 B2 | 8/2014 | Hoffman et al. |
| 8,816,628 B2 | 8/2014 | Nowlin et al. |
| 8,821,480 B2 | 9/2014 | Burbank |
| 8,823,308 B2 | 9/2014 | Nowlin et al. |
| 8,827,989 B2 | 9/2014 | Niemeyer |
| 8,828,023 B2 | 9/2014 | Neff et al. |
| 8,838,270 B2 | 9/2014 | Druke et al. |
| 8,852,174 B2 | 10/2014 | Burbank |
| 8,858,547 B2 | 10/2014 | Brogna |
| 8,862,268 B2 | 10/2014 | Robinson et al. |
| 8,864,751 B2 | 10/2014 | Prisco et al. |
| 8,864,752 B2 | 10/2014 | Diolaiti et al. |
| 8,903,546 B2 | 12/2014 | Diolaiti et al. |
| 8,903,549 B2 | 12/2014 | Itkowitz et al. |
| 8,911,428 B2 | 12/2014 | Cooper et al. |
| 8,912,746 B2 | 12/2014 | Reid et al. |
| 8,944,070 B2 | 2/2015 | Guthart et al. |
| 8,989,903 B2 | 3/2015 | Weir et al. |
| 9,002,518 B2 | 4/2015 | Manzo et al. |
| 9,014,856 B2 | 4/2015 | Manzo et al. |
| 9,016,540 B2 | 4/2015 | Whitman et al. |
| 9,019,345 B2 | 4/2015 | Patrick |
| 9,043,027 B2 | 5/2015 | Durant et al. |
| 9,050,120 B2 | 6/2015 | Swarup et al. |
| 9,055,961 B2 | 6/2015 | Manzo et al. |
| 9,068,628 B2 | 6/2015 | Solomon et al. |
| 9,078,684 B2 | 7/2015 | Williams |
| 9,084,623 B2 | 7/2015 | Gomez et al. |
| 9,095,362 B2 | 8/2015 | Dachs, II et al. |
| 9,096,033 B2 | 8/2015 | Holop et al. |
| 9,101,381 B2 | 8/2015 | Burbank et al. |
| 9,113,877 B1 | 8/2015 | Whitman et al. |
| 9,138,284 B2 | 9/2015 | Krom et al. |
| 9,144,456 B2 | 9/2015 | Rosa et al. |
| 9,198,730 B2 | 12/2015 | Prisco et al. |
| 9,204,923 B2 | 12/2015 | Manzo et al. |
| 9,226,648 B2 | 1/2016 | Saadat et al. |
| 9,226,750 B2 | 1/2016 | Weir et al. |
| 9,226,761 B2 | 1/2016 | Burbank |
| 9,232,984 B2 | 1/2016 | Guthart et al. |
| 9,241,766 B2 | 1/2016 | Duque et al. |
| 9,241,767 B2 | 1/2016 | Prisco et al. |
| 9,241,769 B2 | 1/2016 | Larkin et al. |
| 9,259,275 B2 | 2/2016 | Burbank |
| 9,259,277 B2 | 2/2016 | Rogers et al. |
| 9,259,281 B2 | 2/2016 | Griffiths et al. |
| 9,259,282 B2 | 2/2016 | Azizian et al. |
| 9,261,172 B2 | 2/2016 | Solomon et al. |
| 9,265,567 B2 | 2/2016 | Orban, III et al. |
| 9,265,584 B2 | 2/2016 | Itkowitz et al. |
| 9,283,049 B2 | 3/2016 | Diolaiti et al. |
| 9,301,811 B2 | 4/2016 | Goldberg et al. |
| 9,314,307 B2 | 4/2016 | Richmond et al. |
| 9,317,651 B2 | 4/2016 | Nixon |
| 9,345,546 B2 | 5/2016 | Toth et al. |
| 9,393,017 B2 | 7/2016 | Flanagan et al. |
| 9,402,689 B2 | 8/2016 | Prisco et al. |
| 9,417,621 B2 | 8/2016 | Diolaiti et al. |
| 9,424,303 B2 | 8/2016 | Hoffman et al. |
| 9,433,418 B2 | 9/2016 | Whitman et al. |
| 9,446,517 B2 | 9/2016 | Burns et al. |
| 9,452,020 B2 | 9/2016 | Griffiths et al. |
| 9,474,569 B2 | 10/2016 | Manzo et al. |
| 9,480,533 B2 | 11/2016 | Devengenzo et al. |
| 9,503,713 B2 | 11/2016 | Zhao et al. |
| 9,550,300 B2 | 1/2017 | Danitz et al. |
| 9,554,859 B2 | 1/2017 | Nowlin et al. |
| 9,566,124 B2 | 2/2017 | Prisco et al. |
| 9,579,164 B2 | 2/2017 | Itkowitz et al. |
| 9,585,641 B2 | 3/2017 | Cooper et al. |
| 9,615,883 B2 | 4/2017 | Schena et al. |
| 9,623,563 B2 | 4/2017 | Nixon |
| 9,623,902 B2 | 4/2017 | Griffiths et al. |
| 9,629,520 B2 | 4/2017 | Diolaiti |
| 9,662,177 B2 | 5/2017 | Weir et al. |
| 9,664,262 B2 | 5/2017 | Donlon et al. |
| 9,687,312 B2 | 6/2017 | Dachs, II et al. |
| 9,700,334 B2 | 7/2017 | Hinman et al. |
| 9,718,190 B2 | 8/2017 | Larkin et al. |
| 9,730,719 B2 | 8/2017 | Brisson et al. |
| 9,737,199 B2 | 8/2017 | Pistor et al. |
| 9,795,446 B2 | 10/2017 | DiMaio et al. |
| 9,797,484 B2 | 10/2017 | Solomon et al. |
| 9,801,690 B2 | 10/2017 | Larkin et al. |
| 9,814,530 B2 | 11/2017 | Weir et al. |
| 9,814,536 B2 | 11/2017 | Goldberg et al. |
| 9,814,537 B2 | 11/2017 | Itkowitz et al. |
| 9,820,823 B2 | 11/2017 | Richmond et al. |
| 9,827,059 B2 | 11/2017 | Robinson et al. |
| 9,830,371 B2 | 11/2017 | Hoffman et al. |
| 9,839,481 B2 | 12/2017 | Blumenkranz et al. |
| 9,839,487 B2 | 12/2017 | Dachs, II |
| 9,850,994 B2 | 12/2017 | Schena |
| 9,855,102 B2 | 1/2018 | Blumenkranz |
| 9,855,107 B2 | 1/2018 | Labonville et al. |
| 9,872,737 B2 | 1/2018 | Nixon |
| 9,877,718 B2 | 1/2018 | Weir et al. |
| 9,883,920 B2 | 2/2018 | Blumenkranz |
| 9,888,974 B2 | 2/2018 | Niemeyer |
| 9,895,813 B2 | 2/2018 | Blumenkranz et al. |
| 9,901,408 B2 | 2/2018 | Larkin |
| 9,918,800 B2 | 3/2018 | Itkowitz et al. |
| 9,943,375 B2 | 4/2018 | Blumenkranz et al. |
| 9,948,852 B2 | 4/2018 | Lilagan et al. |
| 9,949,798 B2 | 4/2018 | Weir |
| 9,949,802 B2 | 4/2018 | Cooper |
| 9,952,107 B2 | 4/2018 | Blumenkranz et al. |
| 9,956,044 B2 | 5/2018 | Gomez et al. |
| 9,980,778 B2 | 5/2018 | Ohline et al. |
| 9,987,094 B2 | 6/2018 | Allen et al. |
| 10,008,017 B2 | 6/2018 | Itkowitz et al. |
| 10,028,793 B2 | 7/2018 | Griffiths et al. |
| 10,033,308 B2 | 7/2018 | Chaghajerdi et al. |
| 10,034,719 B2 | 7/2018 | Richmond et al. |
| 10,052,167 B2 | 8/2018 | Au et al. |
| 10,085,811 B2 | 10/2018 | Weir et al. |
| 10,092,344 B2 | 10/2018 | Mohr et al. |
| 10,123,844 B2 | 11/2018 | Nowlin et al. |
| 10,188,471 B2 | 1/2019 | Brisson |
| 10,201,390 B2 | 2/2019 | Swarup et al. |
| 10,213,202 B2 | 2/2019 | Flanagan et al. |

(56) References Cited

U.S. PATENT DOCUMENTS

| | | | |
|---|---|---|---|
| 10,258,416 B2 | 4/2019 | Mintz et al. | |
| 10,278,782 B2 | 5/2019 | Jarc et al. | |
| 10,278,783 B2 | 5/2019 | Itkowitz et al. | |
| 10,282,881 B2 | 5/2019 | Itkowitz et al. | |
| 10,335,183 B2 | 7/2019 | Worrell et al. | |
| 10,335,242 B2 | 7/2019 | Devengenzo et al. | |
| 10,405,934 B2 | 9/2019 | Prisco et al. | |
| 10,433,922 B2 | 10/2019 | Itkowitz et al. | |
| 10,464,219 B2 | 11/2019 | Robinson et al. | |
| 10,485,621 B2 | 11/2019 | Morrissette et al. | |
| 10,500,004 B2 | 12/2019 | Hanuschik et al. | |
| 10,500,005 B2 | 12/2019 | Weir et al. | |
| 10,500,007 B2 | 12/2019 | Richmond et al. | |
| 10,507,066 B2 | 12/2019 | DiMaio et al. | |
| 10,507,068 B2* | 12/2019 | Kopp | G01R 31/343 |
| 10,510,267 B2 | 12/2019 | Jarc et al. | |
| 10,524,871 B2 | 1/2020 | Liao | |
| 10,548,459 B2 | 2/2020 | Itkowitz et al. | |
| 10,575,909 B2 | 3/2020 | Robinson et al. | |
| 10,592,529 B2 | 3/2020 | Hoffman et al. | |
| 10,595,946 B2 | 3/2020 | Nixon | |
| 10,881,469 B2 | 1/2021 | Robinson | |
| 10,881,473 B2 | 1/2021 | Itkowitz et al. | |
| 10,898,188 B2 | 1/2021 | Burbank | |
| 10,898,189 B2 | 1/2021 | McDonald, II | |
| 10,905,506 B2 | 2/2021 | Itkowitz et al. | |
| 10,912,544 B2 | 2/2021 | Brisson et al. | |
| 10,912,619 B2 | 2/2021 | Jarc et al. | |
| 10,918,387 B2 | 2/2021 | Duque et al. | |
| 10,918,449 B2 | 2/2021 | Solomon et al. | |
| 10,932,870 B2 | 3/2021 | Kopp et al. | |
| 10,932,873 B2 | 3/2021 | Griffiths et al. | |
| 10,932,877 B2 | 3/2021 | Devengenzo et al. | |
| 2003/0055584 A1* | 3/2003 | Raftari | B60W 10/08 903/906 |
| 2004/0034282 A1* | 2/2004 | Quaid, III | A61B 34/32 600/300 |
| 2005/0131415 A1 | 6/2005 | Hearn et al. | |
| 2008/0272725 A1 | 11/2008 | Bojrup | |
| 2010/0018066 A1* | 1/2010 | Kipnes | G01B 3/48 340/665 |
| 2010/0145521 A1* | 6/2010 | Prisco | A61B 34/70 700/264 |
| 2010/0251846 A1 | 10/2010 | Pick et al. | |
| 2011/0166745 A1 | 7/2011 | Tiwari et al. | |
| 2012/0116416 A1 | 5/2012 | Neff et al. | |
| 2013/0266110 A1 | 10/2013 | Yanagisawa | |
| 2013/0317519 A1 | 11/2013 | Romo et al. | |
| 2014/0039517 A1 | 2/2014 | Bowling et al. | |
| 2014/0371751 A1 | 12/2014 | Thomas | |
| 2017/0312039 A1* | 11/2017 | Crawford | A61B 17/1604 |
| 2018/0049814 A1* | 2/2018 | Overmyer | A61B 34/35 |

FOREIGN PATENT DOCUMENTS

| | | |
|---|---|---|
| JP | 2007195993 A | 8/2007 |
| WO | 03101322 A1 | 12/2003 |
| WO | 2015120108 | 8/2015 |

OTHER PUBLICATIONS

Japanese Notice of Allowance corresponding to counterpart Patent Application No. JP 2017-565238 dated Aug. 3, 2020; and machine generated EnglishTranslation.

Chinese First Office Action dated Mar. 12, 2020 corresponding to counterpart Patent Application CN 201680034888.8.

International Search Report dated Sep. 26, 2016, issued in PCT/US2016/037478.

Written Opinion of the International Searching Authority dated Sep. 26, 2016 in PCT/US2016/037478.

Extended European Search Report corresponding to counterpart Patent Application No. EP 16812268.7 dated Jan. 25, 2019.

Indian Office Action dated Nov. 23, 2020 corresponding to counterpart Patent Application IN 201717045951.

Japanese Office Action dated Jun. 2, 2021 corresponding to counterpart Patent Application JP 2020-116880.

Canadian Office Action dated Oct. 4, 2022 corresponding to counterpart Patent Application CA 2,987,637.

* cited by examiner

ROBOTIC SURGICAL SYSTEM TORQUE TRANSDUCTION SENSING

CROSS-REFERENCE TO RELATED APPLICATIONS

This application is a Continuation application claiming the benefit of and priority to U.S. patent application Ser. No. 16/713,586, filed on Dec. 13, 2019 (now U.S. Pat. No. 10,932,870), which is a Continuation application claiming the benefit of and priority to U.S. patent application Ser. No. 15/579,308, filed on Dec. 4, 2017 (now U.S. Pat. No. 10,507,068), which is a National Stage Application of PCT Application Serial No. PCT/US2016/037478 under 35 USC § 371 (a), filed Jun. 15, 2016, which claims the benefit of and priority to U.S. Provisional Patent Application No. 62/180,124 filed Jun. 16, 2015, the entire disclosure of each of which being incorporated by reference herein.

BACKGROUND

Robotic surgical systems have been used in minimally invasive medical procedures. During such a medical procedure, the robotic surgical system is controlled by a surgeon that interfaces with a user interface. The user interface allows the surgeon to manipulate an end effector that acts on a patient. The user interface has an input controller or handle that is moveable by the surgeon to control the robotic surgical system.

The end effectors of the robotic surgical system are positioned at the end of a surgical instrument that is connected to robotic arms. Each end effector can be manipulated by an Instrument Drive Unit (IDU). An IDU may have a drive motor associated with the end effector and be configured to move the end effector about a respective axis or to actuate a particular function of the end effector (e.g., approximate, pivot, etc. jaws of the end effector).

Safety systems in the robotic surgical system monitored the drive motor current. If the measured motor current exceeded a preset safety threshold a fault would be presumed and the motor would be turned off. These systems had limited ability to detect different types of faults as they did not take into account the actual forces at the motor output.

There is a need for robust instrument drive unit fault detection that is capable of identifying different types of faults beyond those associated with pure high current draw.

SUMMARY

In an aspect of the present disclosure, verifying a torque measurement of a torque transducer of an instrument drive unit may include receiving a verification signal indicative of current drawn by a motor of the instrument drive unit. An acceptable torque range based on the verification signal may be identified. The torque measurement may be compared with the acceptable torque range. The motor may be stopped if the torque measurement is outside the acceptable torque range.

In aspects, the method may include measuring the torque being applied by the motor with a reaction torque transducer that is electrically isolated from the motor. The reaction torque transducer may transmit the torque signal to the controller. The method may also include generating a fault signal when the torque applied by the motor is outside of the acceptable range of torques. Generating the fault signal may include providing feedback to a clinician in the form of audible, visual, or haptic feedback to the clinician.

In some aspects, a sensor may transmit the verification signal to the controller. A sensor may measure current drawn by the motor to generate the verification signal.

In another aspect of the present disclosure, a control circuit for a motor of an instrument drive unit includes a sensor, a reaction torque transducer, and a controller. The sensor is configured to detect current drawn by the motor and the reaction torque transducer is configured to detect torque applied by the motor. The controller is in communication with the sensor and the reaction torque transducer and is configured to control the motor. The controller is configured to compare the detected current drawn by the motor to the detected torque applied by the motor to verify the detected torque is within an acceptable range of torque values for detected current drawn by the motor.

In aspects, the control circuit includes a motor energy source that is in electrical communication with the motor. The motor energy source may be electrically isolated from the reaction torque transducer. The sensor may be configured to detect current drawn by the motor from the motor energy source.

In some aspects, the reaction torque transducer is configured to detect a mechanical property induced by torque applied by the motor. The mechanical property may be strain.

In another aspect of the present disclosure, an instrument drive unit of a robotic surgical system includes a fixed plate, a first motor, a first reaction torque transducer, a first sensor, and a first controller. The first motor has a first drive shaft and the first reaction torque transducer is disposed about the first drive shaft to secure the first motor to the fixed plate. The first reaction torque transducer is configured to detect torque delivered by the first motor. The first sensor is configured to detect current drawn by the first motor. The first controller is configured to control the first motor. The first controller is in communication with the first sensor and the first reaction torque transducer. The first controller is configured to compare the detected current drawn by the first motor to the detected torque delivered by the first motor to verify that the detected torque is within an acceptable range of torque values for the detected current drawn by the first motor.

In aspects, the instrument drive unit includes a second motor, a second reaction torque transducer, and a second sensor. The second motor has a second drive shaft and the second reaction torque transducer is disposed about the second drive shaft to secure the second motor to the fixed plate. The second reaction torque transducer is configured to detect torque delivered by the second motor. The second sensor is configured to detect current drawn by the second motor. The first controller is configured to control the second motor. The first controller is in communication with the second sensor and the second reaction torque transducer. The first controller is configured to compare the detected current drawn by the second motor to the detected torque delivered by the second motor to verify that the detected torque is within an acceptable range of torque values for the detected current drawn by the second motor.

In some aspects, the instrument drive unit includes a third motor, a third reaction torque transducer, a third sensor, and a second controller. The third motor has a third drive shaft and the third reaction torque transducer is disposed about the third drive shaft to secure the third motor to the fixed plate. The third reaction torque transducer is configured to detect torque delivered by the third motor. The third sensor is configured to detect current drawn by the third motor. The second controller is configured to control the third motor.

The second controller is in communication with the third sensor and the third reaction torque transducer. The second controller is configured to compare the detected current drawn by the third motor to the detected torque delivered by the third motor to verify that the detected torque is within an acceptable range of torque values for the detected current drawn by the third motor.

Further details and aspects of exemplary embodiments of the present disclosure are described in more detail below with reference to the appended figures.

BRIEF DESCRIPTION OF THE DRAWINGS

Various aspects of the present disclosure are described hereinbelow with reference to the drawings, which are incorporated in and constitute a part of this specification, wherein.

DETAILED DESCRIPTION

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" refers to the portion of the device or component thereof that is closest to the clinician and the term "distal" refers to the portion of the device or component thereof that is farthest from the clinician.

The present disclosure generally relates to an instrument drive unit (IDU) for a robotic surgical system that includes a torque transducer (e.g., primary sensor) that measures the torque applied by a motor and provides a torque signal to a controller that drives the motor. The IDU also includes a secondary sensor that measures an input to the motor to provide a verification signal to the controller. The controller compares the torque signal and the verification signal to ensure the torque transducer is functioning properly. If the torque signal is outside of an acceptable range of values for a given verification signal, the controller generates a fault signal and/or stops the robotic surgical system.

As detailed herein, the IDU includes a reaction torque transducer as the primary sensor. However, it is contemplated that the primary sensor may be an inline torque transducer.

Figure 1:
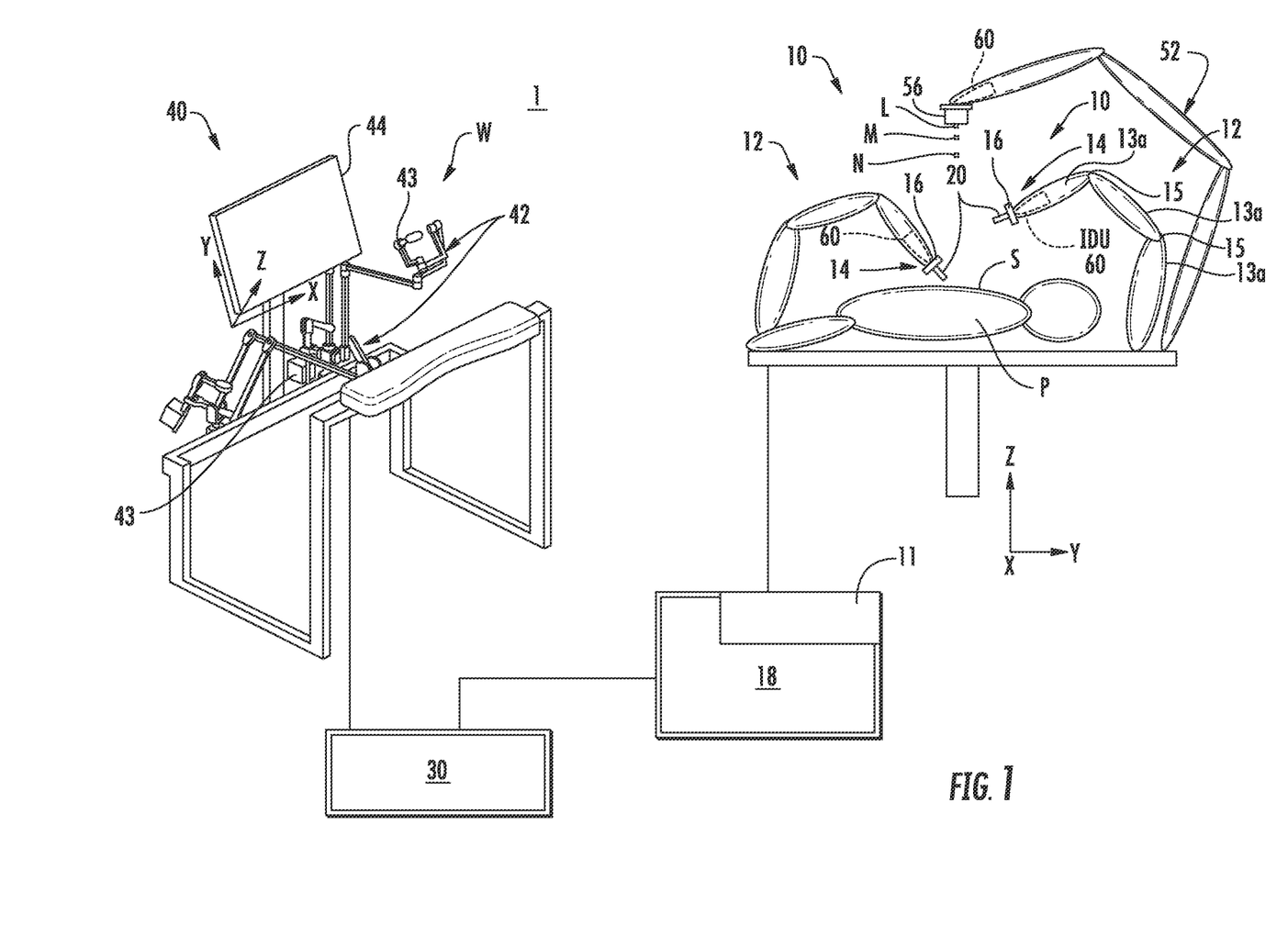
FIG. 1 is a schematic illustration of a user interface and a robotic system.

Referring to FIG. 1, a robotic surgical system 1, is shown and includes a robotic system 10, a processing unit 30, and a user interface 40. The robotic system 10 generally includes linkages 12 and a robot base 18. The linkages 12 moveably support a surgical instrument having an end effector or tool 20 which is configured to act on tissue. The linkages 12 may be in the form of arms each having a plurality of members 13. A member 13a of the plurality of members 13 has an end 14 that supports end effector or tool 20 which is configured to act on tissue. In addition, the end 14 of the member 13a may include an imaging device 16 for imaging a surgical site "S". Each of the plurality of members 13 of the linkages 12 may be connected to one another about joints 15. The user interface 40 is in communication with robot base 18 through the processing unit 30.

The user interface 40 includes a display device 44 which is configured to display three-dimensional images. The display device 44 displays three-dimensional images of the surgical site "S" which may include data captured by imaging devices 16 positioned on the end 14 of the member 13a and/or include data captured by imaging devices that are positioned about the surgical theater (e.g., an imaging device positioned within the surgical site "S", an imaging device positioned adjacent the patient "P", imaging device 56 positioned at a distal end of an imaging arm 52). The imaging devices (e.g., imaging devices 16, 56) may capture visual images, infra-red images, ultrasound images, X-ray images, thermal images, and/or any other known real-time images of the surgical site "S". The imaging devices transmit captured imaging data to the processing unit 30 which creates three-dimensional images of the surgical site "S" in real-time from the imaging data and transmits the three-dimensional images to the display device 44 for display.

The user interface 40 also includes input handles 42 which allow a clinician to manipulate the robotic system 10 (e.g., move the linkages 12, the ends 14 of the linkages 12, and/or the tools 20). Each of the input handles 42 is in communication with the processing unit 30 to transmit control signals thereto and to receive feedback signals therefrom. Each of the input handles 42 may include input devices which allow the surgeon to manipulate (e.g., clamp, grasp, fire, open, close, rotate, thrust, slice, etc.) the tools 20 supported at the end 14 of the member 13a.

For a detailed discussion of the construction and operation of a robotic surgical system 1, reference may be made to U.S. Patent Publication No. 2012/0116416, entitled "Medical Workstation," now U.S. Pat. No. 8,828,023.

Figure 2:
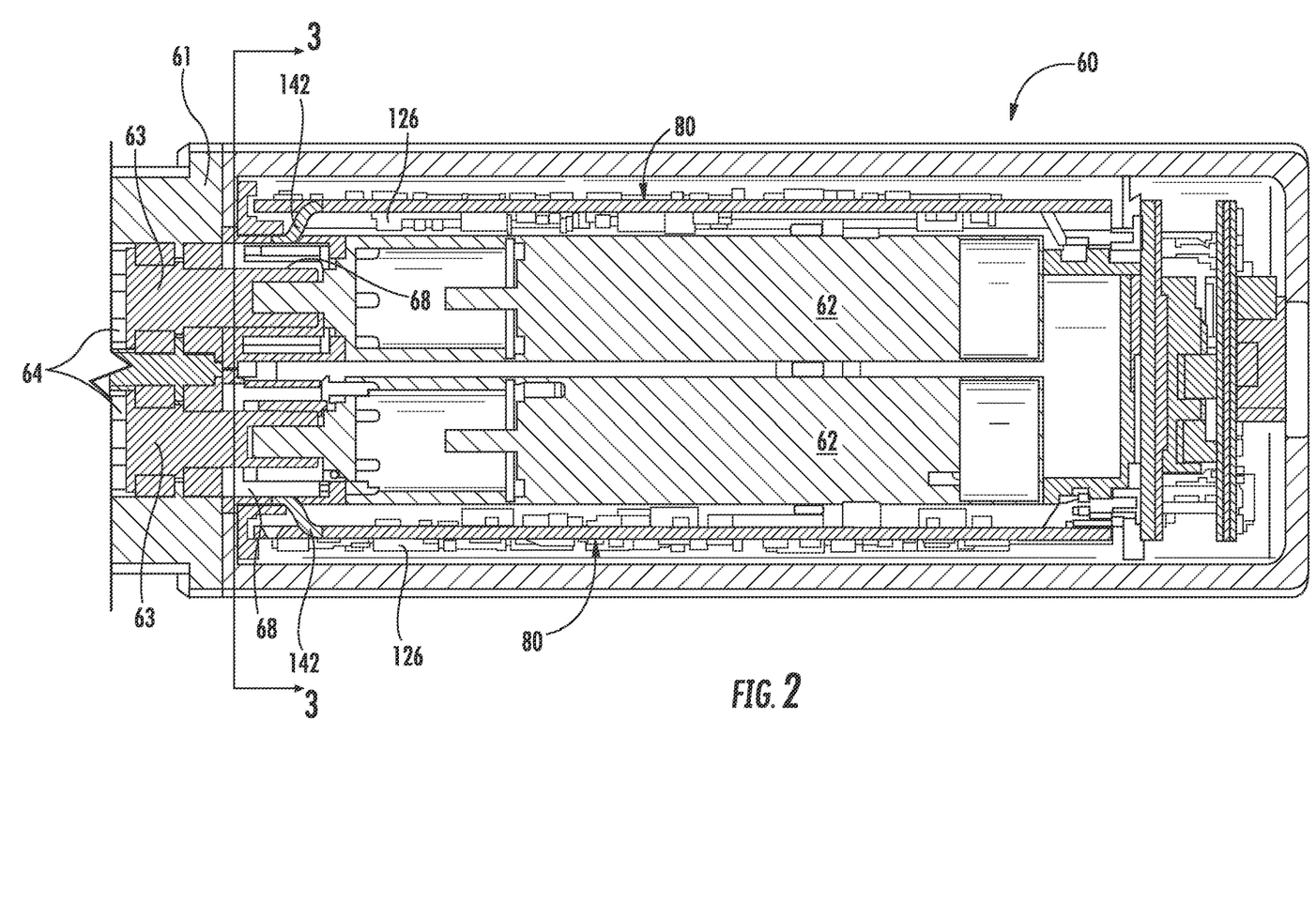
FIG. 2 is a side, cross-sectional view of an instrument drive unit of the robotic system of FIG. 1.
Figure 3:
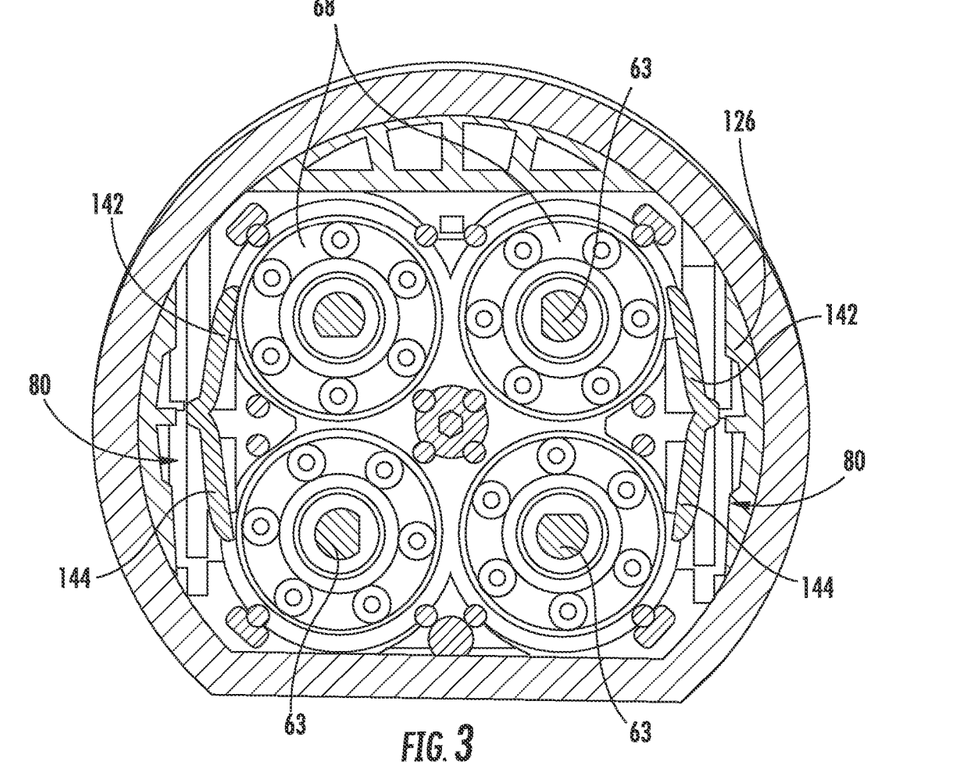
FIG. 3 is a cross-sectional view taken along the section line 3-3 of FIG. 2.

Referring also to FIGS. 2 and 3, an instrument drive unit (IDU) 60 is disposed within or supported on the member 13a adjacent the end 14. The IDU 60 is operatively associated with a tool 20 coupled to the end 14 to manipulate the tool 20 in response to tool signals transmitted from the processing unit 30. The IDU 60 includes motors 62 which are each operably coupled to a respective converter 64 and a respective reaction torque transducer 68. Each motor 62 rotates a drive shaft 63 that extends through a primary sensor or reaction torque transducer 68 in response to energy supplied to the motor 62. The converter 64 converts rotation of the drive shaft 63 of the motor 62 to linear movement of a drive rod and/or cable (not shown). The converter 64 may be secured to a fixed plate 61 of the IDU 60. The reaction torque transducer 68 measures torque applied or delivered by the motor 62 to the converter 64 and thus, measures force applied to the tools 20. The reaction torque transducer 68 is positioned about the drive shaft 63 of the motor 62 and secures the motor 62 to the fixed plate 61 of the IDU 60.

For a detailed discussion of the construction and operation of the reaction torque transducer 68, reference may be made to International Patent Application No. PCT/US15/14542, filed on Feb. 5, 2015, and entitled "Input Device Assemblies for Robotic Surgical Systems", now U.S. Pat. No. 9,987,094, the entire contents of which are incorporated herein by reference.

With reference to FIGS. 2 and 3, the IDU 60 includes one or more circuit boards 80 that each include a controller 126 which are provided in accordance with the present disclosure. As detailed below, the controllers 126 are detailed in terms of a singular controller 126; however, it will be appreciated that the IDU 60 may have one or more controllers 126. The controller 126 is in communication with one or more reaction torque transducers 68. As shown, the controller 126 is in communication with a reaction torque transducer 68 by a lead 142 and another reaction torque transducer 68 by a lead 144. Each lead 142, 144 carries a torque signal indicative of torque being applied by the motor 62 sensed by the respective torque transducer 68 to the controller 126.

While the torque being applied by the motor 62 may be precisely measured by the reaction torque transducer 68, the torque being applied by the motor 62 can also be calculated from the amount of current drawn by the motor 62. As detailed below, this calculated torque can be used to verify that the measured torque (i.e., torque detected by the reaction torque transducer 68) is within an acceptable range of values for a detected amount of current drawn by the motor 62. By verifying that the detected torque is in the acceptable range of values for a detected amount of current drawn, a fault may be generated and/or the motor 62 may be stopped if the detected torque is outside of the acceptable range of values for a detected amount of current drawn. It will be understood that when the detected torque is outside of the acceptable range of values for a detected amount of current drawn that the reaction torque transducer 68 may have failed.

Continuing to refer to FIGS. 2 and 3, the IDU 60 includes sensors 152, 154 that provide verification signals to the circuit board 80. The sensors 152, 154 are each associated with a respective motor 62 to detect an amount of current drawn by the respective motor 62. Each sensor 152, 154 then sends a respective verification signal to the controller 126 indicative of the amount of current drawn by the respective motor 62. The controller 126 compares the verification signal to the torque signal to verify that the torque signal is within an acceptable range of values with respect to the verification signal.

It is contemplated that the sensors 152, 154 may detect a torque and generate a current from the detected current. In such embodiments, the controller compares the current of the verification signal to the torque signal to verify that the torque signal is within an acceptable range of values with respect to the verification signal.

Figure 4:
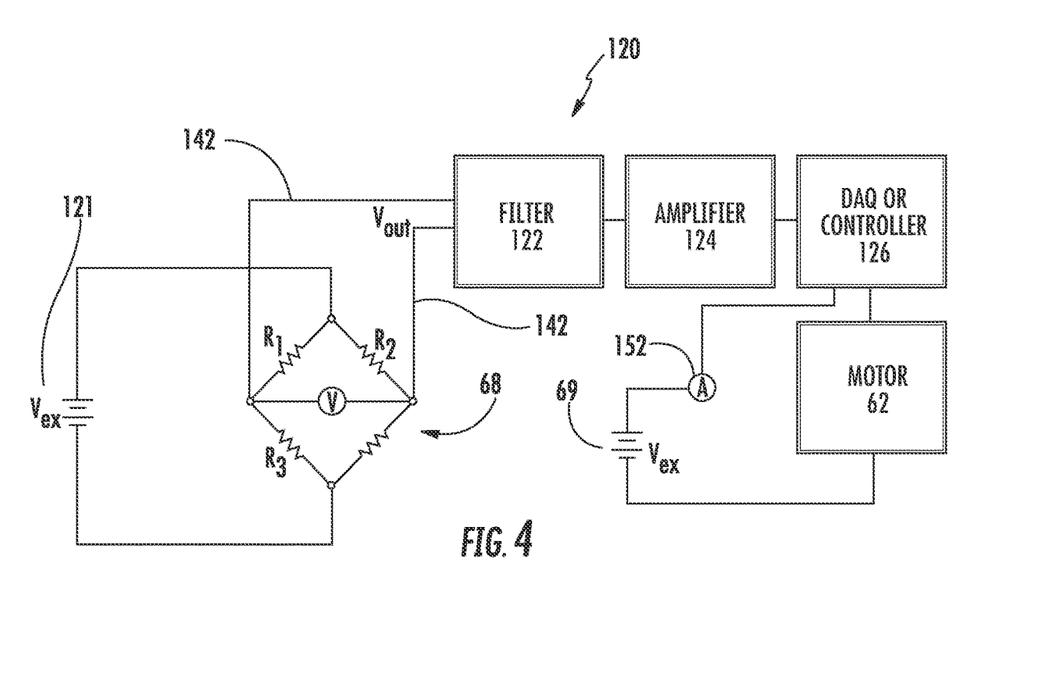
FIG. 4 is a schematic illustration of a control circuit of the instrument drive unit of FIG. 2.

With reference to FIG. 4, a control circuit 120 compares the torque signal to the verification signal to verify that the detected torque is within an acceptable range of values for the amount current drawn by the motor 62. The control circuit 120 detects the reaction torque of the motor 62 and detects the amount of current drawn by the motor 62 to verify that the detected torque is within an acceptable range of values for the amount of current drawn by the motor 62.

The control circuit 120 includes the motor 62, the reaction torque transducer 68, a voltage source 121, a filter 122, an amplifier 124, the controller 126, and a sensor 152. The reaction torque transducer 68 generates a torque signal that is carried by the leads 132 to the filter 122. The filter 122 is a low pass filter to remove noise from the torque signal. The filter 122 transmits the filtered torque signal to the amplifier 124 which transmits the amplified filtered torque signal to the controller 126. The controller 126 determines the reaction torque of the motor 62 from the torque signal.

The controller 126 sends a control signal to control the motor 62 (e.g., the rotational speed of the motor 62). The controller 126 may send the signal to the motor 62 or to a motor energy source 69 that supplies energy to the motor 62. As the motor 62 draws energy from the motor energy source 69, the sensor 152 detects the amount of current drawn by the motor 62 from the motor energy source 69. The sensor 152 generates the verification signal which is indicative of the amount of current drawn by the motor 62 and sends the verification signal to the controller 126.

The controller 126 compares the torque signal from the reaction torque transducer 68 with the verification signal from the sensor 152. First, the controller 126 generates an acceptable range of values for the torque being applied by the motor 62 from the verification signal. For example, when the verification signal indicates that the motor 62 is drawing 0.80 amps of current, an acceptable range of values for the torque being applied by the motor 62 is about 0.20 N-m to about 0.030 N-m. It will be understood that as the amount of current drawn by the motor 62 increases, upper and lower limits of the acceptable range of values for the torque being applied by the motor increases. In addition, as the amount of current drawn by the motor 62 increases, the acceptable range of values can increase. If the torque signal is within the acceptable range of values, the controller 126 continues to send a control signal indicative of continued rotation of the motor 62.

When the torque signal is outside of the acceptable range of values, the reaction torque transducer 68 may be malfunctioning and thus, providing inaccurate measurement of the torque being applied by the motor 62, or the tools 20 may have hit an obstruction. Accordingly, if the torque signal is outside of the acceptable range of values, the controller 126 may generate a fault signal and/or send a control signal to stop rotation of the motor 62. The fault signal may provide visual, audible, or haptic feedback to a clinician interfacing with the user interface 40 (FIG. 1).

Figure 5:
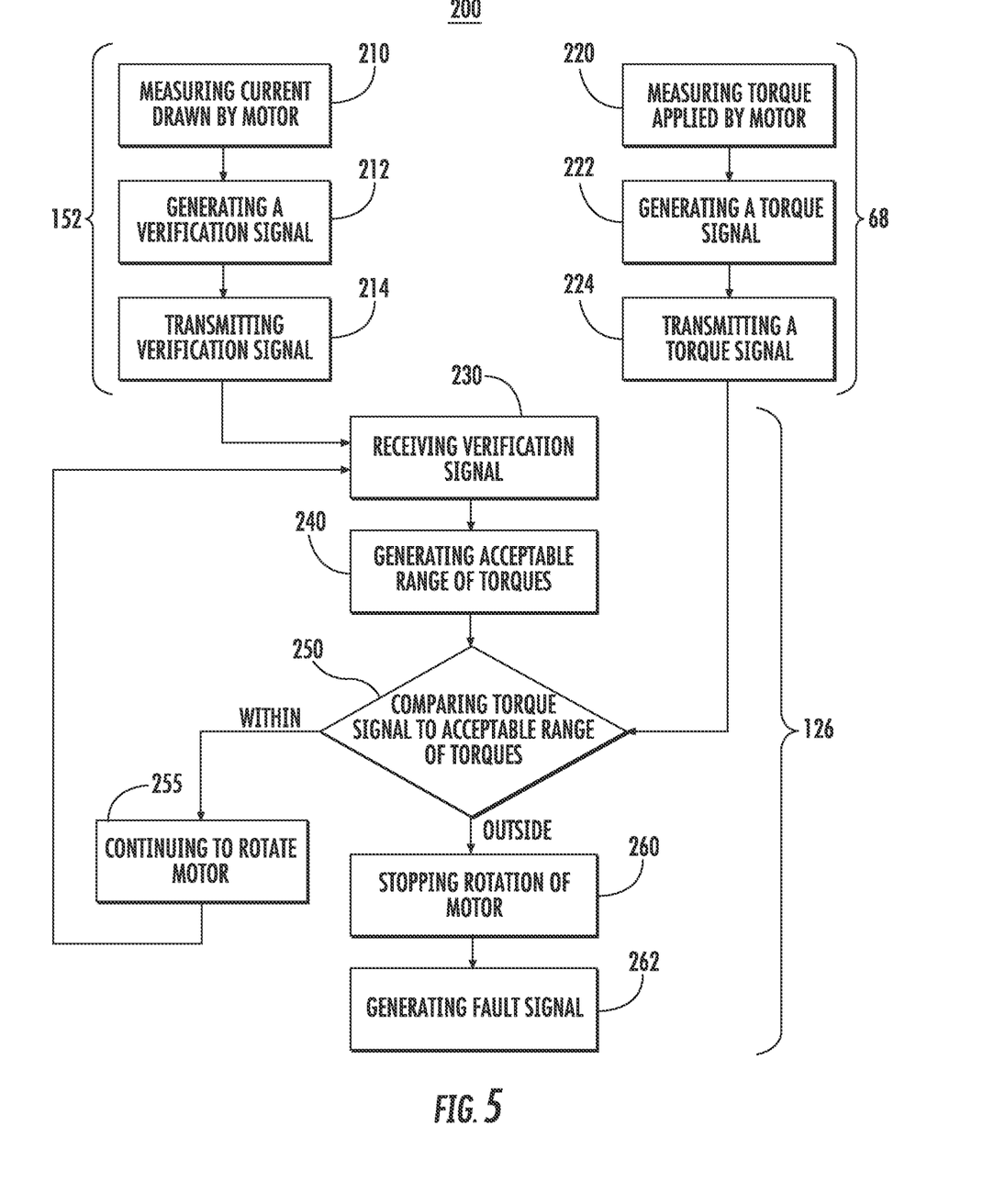
FIG. 5 is a flowchart illustrating a method of controlling the instrument drive unit of FIG. 1.

With reference to FIG. 5, a method 200 of verifying torque measurements of a primary sensor or reaction torque transducer 68 of an instrument drive unit 60 with a sensor 152 is disclosed in accordance with the present disclosure. Initially, the controller 126 receives an instruction signal to rotate the motor 62. In response to the instruction signal, the controller 126 sends a control signal to the motor 62 to rotate the drive shaft 63.

While the motor 62 is rotating, the motor 62 draws current from the motor energy source 69 (FIG. 4). This current is measured by sensor 152 (Step 210). The sensor 152 generates a verification signal indicative of the measured current (Step 212) and transmits the verification signal to the controller 126 (Step 214). In addition, while the motor 62 is rotating, the reaction torque transducer 68 measures torque applied by the motor 62 (Step 220). The reaction torque transducer 68 generates a torque signal indicative of the measured torque (Step 222) and transmits the torque signal to the controller 126 (Step 224).

The controller 126 receives the verification signal (Step 230) and generates an acceptable range of torques which may be applied by the motor 62 for the given verification signal (Step 240). As detailed above, the acceptable range of torques is proportional to current drawn by the motor 62. The controller 126 then receives the torque signal from the reaction torque transducer 68 and compares the torque signal to the acceptable range of torques (Step 250). If the torque signal is within the acceptable range of torques, the controller 126 continues to send a control signal to the motor 62 to rotate the drive shaft 63 (Step 255). In contrast, if the torque signal is outside of the acceptable range of torques, the controller 126 stops rotation of the motor 62 by sending a control signal or ceasing to send a control signal (Step 260). The controller 126 then generates a fault signal indicative of the torque applied by the motor 62 being outside of the acceptable range of torque values. The fault signal may be audible, visual, haptic, or any combination thereof to alert a clinician of the fault.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed:

1. A method of verifying torque measurements of torque transducers of an instrument drive unit of a robotic surgical system, the method comprising:
   detecting a current drawn by a motor of the instrument drive unit;
   sending a verification signal to a controller indicative of the current drawn by the motor;
   detecting a torque delivered by the motor;
   identifying an acceptable range of torque values based on the verification signal sent to the controller;
   comparing the detected current drawn by the motor to the detected torque delivered by the motor to verify that the detected torque delivered by the motor is within the acceptable range of torque values based on the verification signal; and
   stopping the motor when the detected torque delivered by the motor of the instrument drive unit is outside the acceptable range of torque values based on the verification signal.

2. The method according to claim 1, further comprising measuring the torque being delivered by the motor with a reaction torque transducer that is electrically isolated from the motor, the reaction torque transducer transmitting a torque signal indicative of the torque being delivered by the motor to the controller performing the comparing.

3. The method according to claim 1, further comprising generating a fault signal when the detected torque is outside of the acceptable range of torque values.

4. The method according to claim 1, further comprising detecting, with a sensor, the current drawn by the motor.

5. The method according to claim 3, wherein generating the fault signal includes providing feedback to a clinician, the feedback being audible, visual, haptic, or a combination thereof.

6. The method according to claim 4, further comprising generating the verification signal with the sensor, the sensor transmitting the verification signal to the controller.

7. The method according to claim 6, wherein the motor is a first motor, the sensor is a first sensor, the current is a first current, the verification signal is a first verification signal, and the controller is a first controller, the method further comprising:
   detecting, with a second sensor, a second current drawn by a second motor of the instrument drive unit;
   sending a second verification signal to a second controller indicative of the second current drawn by the second motor;
   detecting a torque delivered by the second motor of the instrument drive unit;
   identifying an acceptable range of torque values based on the second verification signal sent to the second controller;
   comparing the detected second current drawn by the second motor to the detected torque delivered by the second motor to verify that the detected torque delivered by the second motor is within the acceptable range of torque values based on the second verification signal; and
   stopping the second motor when the detected torque delivered by the second motor of the instrument drive unit is outside the acceptable range of torque values based on the second verification signal.

8. A control circuit for motors of an instrument drive unit of a robotic surgical system, the control circuit comprising:
   a sensor configured to detect current drawn by a motor of the instrument drive unit;
   a reaction torque transducer configured to detect torque applied by the motor; and
   a controller in communication with the sensor and the reaction torque transducer and configured to control the motor, the controller configured to:
      receive a verification signal that is indicative of the current drawn by the motor;
      receive a torque signal from the reaction torque transducer;
      identify an acceptable range of torque values based on the verification signal; and
      compare the detected current drawn by the motor to the detected torque delivered by the motor to verify that the detected torque delivered by the motor is within the acceptable range of torque values based on the verification signal.

9. The control circuit according to claim 8, wherein the motor is a first motor, the sensor is a first sensor, the current is a first current, the reaction torque transducer is a first reaction torque transducer, and the controller is a first controller, further comprising:
   a second sensor configured to detect current drawn by a second motor of the instrument drive unit;
   a second reaction torque transducer configured to detect torque applied by the second motor; and
   a second controller in communication with the second sensor and the second reaction torque transducer and configured to control the second motor, the second controller configured to:
      receive a second verification signal that is indicative of the current drawn by the second motor;
      receive a second torque signal from the second reaction torque transducer;
      identify an acceptable range of torque values based on the second verification signal; and
      compare the detected current drawn by the second motor to the detected torque delivered by the second motor to verify that the detected torque delivered by the second motor is within the acceptable range of torque values based on the second verification signal.

10. The control circuit according to claim 9, further comprising a motor energy source in electrical communication with the each of the motors, the motor energy source electrically isolated from each reaction torque transducer.

11. The control circuit according to claim 9, wherein each reaction torque transducer is configured to detect a mechanical property induced by torque applied by each respective motor.

12. The control circuit according to claim 10, wherein each sensor is configured to detect a respective current drawn by each motor from the motor energy source.

13. The control circuit according to claim 11, wherein the mechanical property is strain.

14. A method of verifying torque measurements of torque transducers of an instrument drive unit of a robotic surgical system, the method comprising:
- detecting a current drawn by each motor of a plurality of motors of the instrument drive unit;
- sending a verification signal to a controller indicative of each current drawn by each motor of the plurality of motors;
- detecting a torque delivered by each motor of the plurality of motors;
- identifying an acceptable range of torque values for each motor based on the verification signals sent to the controller;
- comparing the detected current drawn by each motor of the plurality of motors to the detected torque delivered by each motor of the plurality of motors to verify that the detected torque delivered by each motor of the plurality of motors is within the acceptable range of torque values based on the verification signals; and
- when the detected torque delivered by an individual motor of the plurality of motors, is outside the acceptable range of torque values based on the respective verification signal, stopping the individual motor of the plurality of motors.

15. The method according to claim 14, further comprising measuring the torque being delivered by the individual motor of the plurality of motors with a respective reaction torque transducer that is electrically isolated from the respective motor, each reaction torque transducer transmitting a torque signal indicative of the torque being delivered by the individual motor of the plurality of motors to the controller performing the comparing.

16. The method according to claim 14, further comprising generating a fault signal when the detected torque for any motor of the plurality of motors is outside of the acceptable range of torque values.

17. The method according to claim 14, further comprising detecting, with a sensor, the current drawn by any motor of the plurality of motors.

18. The method according to claim 16, wherein generating the fault signal includes providing feedback to a clinician, the feedback being audible, visual, haptic, or a combination thereof.

19. The method according to claim 17, further comprising generating the verification signal with the sensor, the sensor transmitting the verification signal to the controller.

20. The method according to claim 19, wherein the plurality of motors includes a first motor, the sensor is a first sensor, the current is a first current, the verification signal is a first verification signal, and the controller is a first controller, the method further comprising:
- detecting, with a second sensor, a second current drawn by a second motor of the plurality of motors of the instrument drive unit;
- sending a second verification signal to a second controller indicative of the second current drawn by the second motor;
- detecting a torque delivered by the second motor of the plurality of motors of the instrument drive unit;
- identifying an acceptable range of torque values based on the second verification signal sent to the second controller;
- comparing the detected second current drawn by the second motor of the plurality of motors to the detected torque delivered by the second motor of the plurality of motors to verify that the detected torque delivered by the second motor of the plurality of motors is within the acceptable range of torque values based on the second verification signal; and
- stopping the second motor of the plurality of motors when the detected torque delivered by the second motor of the plurality of motors of the instrument drive unit is outside the acceptable range of torque values based on the second verification signal.

* * * * *